United States Patent
Dias et al.

(10) Patent No.: US 11,738,342 B2
(45) Date of Patent: *Aug. 29, 2023

(54) BIOSENSOR ACTIVATION AND CONDITIONING METHOD AND SYSTEM

(71) Applicant: MURSLA LIMITED, London (GB)

(72) Inventors: Tomas Miguel De Freitas Dias, Cambridge (GB); Pierre Arsène, London (GB)

(73) Assignee: MURSLA LIMITED, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/763,682

(22) PCT Filed: Oct. 30, 2020

(86) PCT No.: PCT/EP2020/080606
§ 371 (c)(1),
(2) Date: Mar. 25, 2022

(87) PCT Pub. No.: WO2021/084116
PCT Pub. Date: May 6, 2021

(65) Prior Publication Data
US 2022/0326231 A1 Oct. 13, 2022

(30) Foreign Application Priority Data

Nov. 1, 2019 (GB) .................................. 1915947
Nov. 1, 2019 (GB) .................................. 1915949

(51) Int. Cl.
*G01N 27/327* (2006.01)
*B01L 3/00* (2006.01)
(Continued)

(52) U.S. Cl.
CPC ... *B01L 3/502715* (2013.01); *B01L 3/502761* (2013.01); *B03C 5/005* (2013.01);
(Continued)

(58) Field of Classification Search
CPC ....................... G01N 33/5438; G01N 27/3278
See application file for complete search history.

(56) References Cited

U.S. PATENT DOCUMENTS 6,333,200 B1  12/2001  Kaier
2002/0123048 A1  9/2002  Gau
(Continued)

FOREIGN PATENT DOCUMENTS

GB  2392977 A  3/2004
GB  2476235 A  6/2011
(Continued)

OTHER PUBLICATIONS

Leiterer et al., Assembling gold nanoparticle chains using an AC electrical field: Electrical detection of organic thiols, 2013, Sensors and Actuators B: Chemical, vol. 176, pp. 368-373. (Year: 2013).*
(Continued)

*Primary Examiner* — Bao-Thuy L Nguyen
*Assistant Examiner* — Jennifer H. Tieu
(74) *Attorney, Agent, or Firm* — Tarolli, Sundheim, Covell & Tummino L.L.P.

(57) ABSTRACT

A method of detecting a target biological entity in a biofluid using a sensor, wherein the biofluid comprises a plurality of the target biological entities and nanoparticles, the sensor comprising a substrate bearing a pair of electrodes having an affinity with the nanoparticles, and wherein a region between the electrodes defines a sensing region. The method comprises: treating the biofluid with a suspension comprising a plurality of nanoparticles to obtain a treated mixture comprising bound nanoparticle-entity assemblies; introducing the treated mixture to the sensor; conditioning the sensor in the presence of the treated mixture by applying an activation voltage between the electrodes to increase a degree of connection between a surface of the pair of electrodes and at
(Continued)

least one bound nanoparticle-entity assembly in contact with the surface of the pair of electrodes; and detecting the presence of target biological entities by using the pair of electrodes to detect a current through the at least one bound nanoparticle-entity assembly.

10 Claims, 9 Drawing Sheets

(51) Int. Cl.
  *G01N 33/543* (2006.01)
  *B03C 5/00* (2006.01)
  *G01N 27/447* (2006.01)

(52) U.S. Cl.
  CPC ..... *G01N 27/3274* (2013.01); *G01N 27/3276* (2013.01); *G01N 27/3278* (2013.01); *G01N 27/44704* (2013.01); *G01N 33/5438* (2013.01); *G01N 33/54326* (2013.01); *G01N 33/54346* (2013.01); *G01N 33/54386* (2013.01); *B01L 2200/0652* (2013.01); *B01L 2200/0668* (2013.01); *B01L 2300/0636* (2013.01); *B01L 2300/0645* (2013.01); *B01L 2300/0816* (2013.01); *B01L 2300/0819* (2013.01); *B03C 2201/26* (2013.01)

(56) References Cited

U.S. PATENT DOCUMENTS

| | | | |
|---|---|---|---|
| 2003/0073149 | A1 | 4/2003 | Archer |
| 2009/0084686 | A1 | 4/2009 | Wan-Soo |
| 2009/0200170 | A1* | 8/2009 | Flanders .................. C25D 1/00 977/899 |
| 2010/0301311 | A1 | 12/2010 | Oku |
| 2018/0059101 | A1 | 3/2018 | Mackay |
| 2020/0116640 | A1* | 4/2020 | Suresh .............. G01N 33/5438 |

FOREIGN PATENT DOCUMENTS

| | | |
|---|---|---|
| KR | 20110080229 A | 7/2011 |
| KR | 20120038804 A | 4/2012 |
| WO | 20060088425 A | 8/2006 |
| WO | 20080020813 A | 2/2008 |
| WO | 20090005542 A2 | 1/2009 |
| WO | 20090023857 A1 | 2/2009 |
| WO | 20130074037 A1 | 5/2013 |
| WO | 20190059961 A1 | 3/2019 |
| WO | 20190211622 A1 | 11/2019 |

OTHER PUBLICATIONS

International Search Report and Written Opinion issued in connection with corresponding patent application No. PCT/EP2020/080606 dated Feb. 24, 2021.
Park, Hyung et al., "High voltage-derived enhancement of electric conduction in nanogap devices for detection of prostate-specific antigen", Applied Physics Letters, vol. 97, No. 3, Jul. 20, 2010, pp. 33701-33701, XP01238472.
Chen X et al., "Electrical nanogap devices for biosensing", Materials Today, Elsevier, Amsterdam, NL, vol. 13, No. 11, Nov. 1, 2010, pp. 28-41, XP027448952.
Jamshaid et al., "Magnetic particles: From preparation to lab-on-a-chip, biosensors, microsystems and microfluidics applications", Trends in Analytical Chemistry, vol. 79, May 1, 2016, pp. 344-362, XP055604195.
Search Report issued in connection with corresponding Great Britain Application No. 1915947.4 dated Jul. 10, 2020.
Search Report issued in connection with corresponding Great Britain Application No. 1915949.0 dated May 1, 2020.
Search Report issued in connection with corresponding Great Britain Application No. 2112518.2 dated Sep. 16, 2021.
International Search Report issued in connection with corresponding patent application No. PCT/GB2019/051233 dated Jul. 12, 2019.
Search Report issued in connection with corresponding Great Britain Application No. 1807293.4 dated Dec. 20, 2018.
Park et al., Applied Physics Letters, vol. 97, "High voltage-derived enhancement of electric conduction in nanogap devices for detection of prostate-specific antigen".

* cited by examiner

BIOSENSOR ACTIVATION AND CONDITIONING METHOD AND SYSTEM

RELATED APPLICATIONS

The present invention is a U.S. National Stage under 35 USC 371 patent application, claiming priority to Serial No. PCT/EP2020/080606, filed on Oct. 30, 2020; which claims priority from Great Britain Patent Application No. 1915947.4 filed on Nov. 1, 2019 and Great Britain Patent Application No. 1915949.0 filed on Nov. 1, 2019; the entireties of all are hereby incorporated herein by reference.

FIELD OF INVENTION

The present invention generally relates to a method and system of detecting a target biological entity, for example within a biofluid, and in particular a method of preparing a biosensor for use.

BACKGROUND

In the field of diagnostics in the medical industry it is often desirable to be able to detect a biological target entity, which may be symptomatic of some underlying condition, efficiently and using a non-invasive procedure. Although an invasive procedure may typically be more reliable in providing concrete evidence for an underlying condition, it may be costly, inconvenient for a patient, and time consuming. Invasive procedures may include such methods as a tissue biopsy. Therefore, this method is unlikely to be the most efficient method of detection. Moreover, it would typically be necessary for a highly trained medical professional to carry out such an invasive procedure.

A preferred method of detection of some target biological entity would be a so called point-of-care procedure. Point-of-care testing is known in the medical and diagnostic industry, and has the advantages of being quicker, non-invasive and not confined to medical laboratory. Such a procedure may take the form of a liquid biopsy. In other words, a bodily fluid may be quickly and comfortably extracted from a patient. For example, the fluid may be a blood sample. The necessary tests would then ideally be performed upon the biopsy fluid in a portable device able to receive the fluid. Further advantages of this method include that it is cheap, has a quick turnaround for receiving a test result, and may not require the supervision of a highly trained medical professional to the same extent as an invasive procedure.

One important area in the medical diagnostic field is that of early cancer detection, screening, prognosis and therapy follow-up. Current methods of diagnosis may involve the detection of nucleic acids indicative of a particular cancer. Such methods use amplification and/or sequencing technologies which effectively create a profile of an entire DNA or RNA sequence. However, these methods require large reagent consumption, are not suitable for point-of-care integration and are likely to be time-consuming and leave significant environmental footprints. A notable alternative to the time-consuming sequencing and/or amplification technologies is a method which, instead, targets the proteins which are the mediators responsible for regulating the relevant activities for cancer cell proliferation. Such protein mediators may be extracted via a liquid biopsy without the need for an invasive procedure.

There also remains a difficulty of providing a method of treating a surface to allow maximise an adhesion affinity to a particle of interest.

SUMMARY

Aspects and preferred features are set out in the accompanying claims.

According to another aspect there is provided a method of detecting a target biological entity in a biofluid using a sensor, wherein the biofluid comprises a plurality of the target biological entities. The method may comprise treating the biofluid with a suspension comprising a plurality of nanoparticles, in particular metallic nanoparticles e.g. gold nanoparticles, to obtain a treated mixture comprising bound nanoparticle-entity assemblies, introducing to the sensor the treated mixture, and conditioning the sensor in the presence of the treated mixture. The sensor may comprise a substrate bearing a pair of electrodes having an affinity with the nanoparticles, and may have a region between the electrodes defines a sensing region.

The conditioning may comprise applying an activation voltage between the electrodes to increase a degree of connection between a surface of the pair of electrodes and at least one nanoparticle in contact with the surface of the pair of electrodes.

Alternatively, the conditioning may comprise applying another form of activation energy to the electrodes in order to increase a degree of connection between a surface of the pair of electrodes and at least one nanoparticle. For example, the electrodes may be conditioned by application of heat that causes the at least one nanoparticle for soften or melt (or otherwise cause diffusion of the gold atoms in the nanoparticle) and thus fuse with each other and/or fuse together with the material of the electrodes. The heat can be applied via the activation voltage as above, or, the heat may generally be applied by any suitable means, for example exposure to infrared radiation via a lamp or oven and the like.

Generally, any reference to activation of the electrodes in the present disclosure is not limited to an activation voltage, and may additionally or alternatively comprise application of an activation energy such as heat (e.g., infrared radiation).

The method may further comprise detecting the presence of target biological entities by using the pair of electrodes to detect a current through the at least one bound nanoparticle-entity assembly. The current may be detected (and measured) using the activation voltage or a later applied (and generally lower) sensing voltage. The current detected may be 1, 2, 3 or more orders of magnitude greater than a current prior to or at the start of applying the activation voltage.

In implementations, use of an activation phase can facilitate nanoparticle assembly (i.e. target entity) detection, by increasing the current to be detected when a target entity is present by two, three or more orders of magnitude, thus greatly simplifying detection and/or increasing detection sensitivity.

The method of detecting a target biological entity may further comprise characterising the treated mixture, the characterising comprising: applying a nanoparticle sensing voltage between the electrodes; characterizing a response of the sensing region to the nanoparticle sensing voltage to determine treated-mixture characterizing data; and detecting the presence of the target biological entity from the treated mixture characterizing data.

In some implementations the conditioning comprises applying an activation energy such as an activation voltage, or activation heat, sufficient to fuse the nanoparticles into a chain of one or more of the nanoparticles linking the pair of electrodes.

In some implementations the activation voltage, which is generally DC but which may be AC, is applied temporarily, e.g. as a pulse, to condition the sensor prior to characterizing the treated mixture by applying the sensing voltage. The nanoparticle sensing voltage may be applied separately e.g. after an activation voltage pulse, or the activation voltage may be used as the nanoparticle sensing voltage e.g. by monitoring a current driven through the pair of electrodes after applying the activation voltage for an activation period.

The magnitude and an activation period duration of application of the activation voltage may be determined by routine experiment and may depend, inter alia, on the nanoparticle size, electrode gap, nanoparticle material melting point. The voltage magnitude may be reduced where the voltage is applied for longer, provided that the voltage is above a threshold needed.

Fusing of the nanoparticles may be established e.g. by capturing an SEM image of the electrodes of an example sensor after an activation voltage has been applied. However activation of a sensor may also be detected by the 2-3 or more orders of magnitude increase in current flowing between the pair of electrodes through the fused nanoparticle(s). Detection of the activation can be used to imply detection of the presence of nanoparticle assemblies i.e. of functionalised nanoparticles to which target entities are bound.

In some implementations the nanoparticle sensing voltage may be less than the activation voltage i.e. a maximum magnitude of the nanoparticle sensing voltage may be less than the activation voltage.

In some example implementations the activation voltage is greater than 1.5 V e.g. around 5 V, and may be less than a damage threshold for the sensor (which may be e.g. around 7 V). The activation period may be greater than 0.5 seconds e.g. 1-10 seconds e.g. around 3 seconds. The nanoparticle sensing voltage may be less than 5 V or <3 V e.g. in the range 0.5-1.5 V.

Prior to activation a current through the electrodes (when a particle is sensed) may be of order pA or nA and may occasionally reach ~1 µA. After activation the current through the electrodes (when a particle is sensed) may increase by 2, 3 or more e.g. up to 6 orders of magnitude, e.g. to of order mA. Following activation Ohmic behaviour may be seen with a resistance of less than 10 KΩ or less than 1 KΩ as compared with e.g. ~GΩ prior to activation.

In some implementations a biofluid is treated with functionalised nanoparticles to obtain nanoparticle assemblies. Nanoparticles which are not in assemblies may be filtered out (the filtering need not be perfect). Then, an activation energy or activation voltage may be applied to an electrode pair in the filtered biofluid i.e. the biofluid comprising nanoparticle assemblies, optionally also using dielectrophoresis to concentrate the assemblies near the electrodes. The activation energy or voltage can fuse the nanoparticles (assemblies) so that they electrically connect the electrodes e.g. into a link or chain of one or more nanoparticles linking the pair of electrodes. The presence of the assemblies may then be detected by detecting current flowing through the fused nanoparticle(s), where said current may be relatively large e.g. >10 µA, >100 µA, or >1 mA.

A biofluid may generally be any fluid or liquid containing biological entities, for example bodily fluid extracted or derived from a patient or animal, such as any of blood, saliva, blood plasma, and the like. Generally, a biofluid may comprise any substance that can be excreted, secreted, or extracted (e.g., from blood), from a patient or animal. The biofluid is generally or substantially aqueous is nature, and may itself be a solution, suspension, or colloid containing target entities. The target entity may comprise any biologically derived entity from a patient, for example a protein, protein fragment, exosome, and ectosome; this list is not exhaustive.

Nanoparticles are generally functionalised in order that they may become bound with the target entity. However, the element which provides this functional attachment (which for example may comprise Neutravidin, but other functional attachments and/or aptamers may be used) to a target entity may be deleterious for conduction across the electrode gap. In other words, a functionalised nanoparticle seated across the sensing region (e.g. electrode nanogap) conducts current less well (e.g. by around 2 orders of magnitude) than a naked nanoparticle. Advantageously, however, application of an activation voltage above a certain activation threshold (which may be above e.g. 1.5 V) may remove/destroy the functional elements on the surface of the nanoparticles, or cause the metal comprised in the nanoparticle to diffuse over the functional elements. This results in an improved electrical contact between the nanoparticle and electrode. Thus, the functional elements may be effectively removed, or overcome, by application of an activation energy such as heat or an activation voltage, such that effectively a naked nanoparticle remains which has a more intimate/direct (e.g. fused) electrical connection.

In the case of metal nanoparticles and electrodes, the activation causes an improved metal-to-metal connection, once the functionalisation is overcome e.g. diffused over, or removed.

Either or both of the nanoparticles and electrodes may comprise a metal such as gold, or even consist entirely of gold. The substrate may comprise silicon, and may also or alternatively comprise glass, ceramic, or silicon dioxide.

Prior to carrying out the above method to detect/characterize a target entity, the sensor itself may be cleaned/prepared in such a way as to improve the connection produced by the activation. Thus, pre-cleaning of a surface of the substrate and a surface of the electrodes may be performed comprising: using an oxygen plasma to provide a precursor sensor; cleaning the precursor sensor to remove excess oxide from the surface of the electrodes. Then, after removing excess oxide from the surface of the electrodes, the preparation further comprises functionalising the surface of the substrate to decrease a surface energy of the substrate relative to a surface energy of the electrodes to provide an enhanced sensor surface, wherein the enhanced sensor surface promotes congregation of particles in a region between the electrodes. In this way, the surface of the electrode is advantageously free of impurities, which provides for a cleaner connection between nanoparticles and electrodes, resulting in better fusion after the conditioning/activation step.

Therefore, it will be appreciated that there is an advantage to carrying out both the preparation steps involving cleaning/functionalisation, and the conditioning step comprising applying an activation energy (e.g., heat) or voltage across a bridged electrode nanogap.

The method of introducing the treated mixture to the sensor may further comprise applying an electric field to the treated mixture to concentrate the bound nanoparticle-entity assemblies in the sensing region. Advantageously, the electric field may induce a dielectrophoretic force may acting on the nanoparticles, which may increase the momentum (compared to normal incubation) of the nanoparticles towards the electrode sensing region (i.e. the electrode tips). It is believed that this increased momentum of NPs towards the electrode gap may result in enhanced quality of the interface between the nanoparticle and electrodes.

Furthermore, the dielectrophoretic force, induced by DEP, may cause the nanoparticles (and/or bound nanoparticle-entity assemblies) to more reliably and precisely become positioned in the middle of the electrode nanogap, thus ensuring that the presence of the nanoparticle can subsequently be effectively sensed.

The at least one nanoparticle in contact with the surface of the pair of electrodes may comprise a single nanoparticle which bridges the gap between the nanoparticles. Alternatively, multiple nanoparticles may congregate in the region in between the electrodes, forming a multi-nanoparticle bridge. In either case, however, when an activation energy or activation voltage is applied across bridging nanoparticles, the current (and e.g. any heat produced as a result of the current) may cause the nanoparticles to coalesce, and/or may cause a surface of the nanoparticle to fuse or partially fuse with a surface of the electrodes.

Applying the electric field may induces an attractive force acting between the sensing region of the electrodes and the nanoparticle of the bound nanoparticle-entity assemblies, thereby advantageously resulting in a greater concentration of target particles in the vicinity of the electrodes.

Applying the electric field to the treated mixture may comprise applying an AC voltage to a pair of treatment electrodes.

Treating the biofluid to obtain the treated mixture may comprise: introducing the biofluid to the suspension to provide a precursor mixture, wherein each of the plurality of nanoparticles is functionalized so that the nanoparticle is able to bind with the target biological entity to produce a bound nanoparticle-entity assembly; and treating the precursor mixture to separate the bound nanoparticle-entity assemblies from nanoparticles not comprised in one of the bound nanoparticle-entity assemblies to provide the treated mixture.

According to any of the above embodiments, the pair of electrodes separated by a lateral distance of e.g. less than around 200 nm. Further according to any of the above embodiments, a dimension of each of the plurality of nanoparticles may greater than the lateral distance separating the pair of electrodes.

Characterizing a response of the sensing region to the nanoparticle sensing voltage to determine treated mixture characterizing data may comprise identifying whether the sensing region exhibits Ohmic behaviour.

The nanoparticle sensing voltage may be a constant voltage which induces a direct current between the electrodes. The plurality of nanoparticles may comprise gold nanoparticles.

According to one aspect there is provided a method of preparing a sensor for detecting a target biological entity in a biofluid, the sensor comprising a substrate bearing a pair of electrodes, wherein the substrate comprises silicon and the electrode comprises a metal. The method comprises: performing a pre-cleaning of a surface of the substrate and a surface of the electrodes using e.g. a plasma or ozone to provide a precursor sensor. The method may further comprise cleaning the precursor sensor to remove excess hydroxyl from the surface of the electrodes. The method may further comprise, after removing excess hydroxyl from the surface of the electrodes, functionalising the surface of the substrate to decrease a surface energy of the substrate relative to a surface energy of the electrodes to provide an enhanced sensor surface.

In implementations, the enhanced sensor surface promotes congregation of particles in a region between the electrodes. For example it is believed that a surface preparation as described above changes a surface energy of the electrodes and or substrate which in turn makes it more likely that target biological entities are found in the vicinity of (tips of the) the pair of electrodes. This is particularly the case when the target biological entities are bound to nanoparticles, in particular metallic nanoparticles. This may be achieved by treating the biofluid with a suspension comprising a plurality nanoparticles to obtain a treated mixture comprising bound nanoparticle-entity assemblies.

The pair of electrodes may be separated by a lateral distance of less than 200 nm. The substrate may comprise one or more of: silicon dioxide, glass, and ceramic.

The pre-cleaning step may comprise exposing the surface of the sensor to oxygen plasma. Alternatively, other forms of plasma may be used, or Ozone in the presence of UV, which may be used to produce Oxygen radicals also perform a cleaning of the sensor surface. Following the plasma clean (which may comprise oxygen, optionally as an $O_2$ plasma, or UV irradiated Ozone) the surface of the silicon substrate may become terminated in hydroxyl groups, either over the whole or a portion of the surface.

It will be understood that an increase in surface energy correlates to a decrease in hydrophobicity. Advantageously, the difference in surface energy of the substrate relative to a surface energy of the electrodes promotes or encourages nanoparticle congregation/adsorption/adhesion at the electrode surface, and in particular the region between the electrodes, which may define a sensing region of the electrodes.

The cleaning may comprise exposing the sensor to a cleaning agent comprising ethanol. The functionalising of the surface of the substrate may comprise exposing the sensor to a functionalisation agent, which reacts with residual hydroxyl on the surface of the substrate to form a coating having a lower surface energy relative to the surface energy of the electrodes. It will be understood therefore that, at each site on the substrate containing residual hydroxyl (i.e. an OH functional group linked to a Si atom), the functionalisation agent reacts to form a further functional group.

The functionalisation agent may be hexamethyldisilazane, HMDS. For example, when HMDS is used, each oxide on the Si substrate surface will form a further siloxane (Si—O—Si) link, which advantageously forms an exposed $Si(CH_3)_3$ group, which collectively form a coating which is hydrophobic (i.e. has low surface energy).

Nevertheless, it will be understood that many suitable alternatives to HMDS may be used, for example, any suitable agent which can react with oxides on a silicon surface to produce a hydrophobic coating. Such alternatives may include other organosilicon compounds or suitable Silane derivatives.

As an alternative to, or indeed in addition to, functionalising the surface with a functionalising agent, the sensors may be stored, e.g. left to stand or rest, for a period of time. Preferably, the storage time should be a matter of days, for example at least one day, or in some examples around 3 days.

Additionally, the storage may be done under vacuum or partial vacuum conditions. A partial vacuum may be defined as any conditions with an air pressure of less than 1 atmosphere, and any reference to vacuum or vacuum conditions in the present disclosure may be interpreted as such. Preferably, however, vacuum conditions in the present disclosure may be around 0.5 bars of pressure, or less. In examples, the storage conditions may also be made substantially free of moisture, for example storage in a desiccator, or vacuum desiccator. The vacuum conditions may provide the advantage of an more inert atmosphere than standard pressure conditions, thereby preventing any unwanted oxidation of the substrate.

Preferably, as mentioned, the sensors should be stored for a period of at least several days, for example at least 3 days. The storage promotes the decrease in surface energy of the substrate, e.g. the recovery of the substrate wherein hydroxyl groups disengage with the substrate. Without wishing to be bound by theory, it appears that removal of hydroxyl groups present on the surface of the (silicon) substrate naturally occurs during a period of rest or storage. Additionally, again without wishing to be bound by theory, it appears that vacuum conditions protect the substrate and electrodes from further oxidation and/or degradation in general. Advantageously, a period of storage allows a scalable approach in which arrays of sensors may be simultaneously treated to decrease surface energy (increase hydrophobicity) of the substrate surface. Moreover, in examples that employ vacuum storage, methods of vacuum storage are scalable in the same manner.

Generally, the disclosed preparation method provides two advantageous effects. The first is to remove impurities on the electrode surface (by virtue of the $O_2$ plasma step), which allows more stable/reliable attraction and connection between a particles (e.g. a nanoparticle) and a surface of the electrode. The second advantage is to provide a difference in surface energies between the substrate and electrode, which alters the surface tension of a fluid in the surrounding region to encourage congregation of particles (contained in the fluid) around only the electrode.

According to another aspect there is provided a method of preparing a sensor for detecting a target biological entity in a biofluid, the sensor comprising a substrate bearing a pair of electrodes, wherein the substrate comprises silicon and the electrode comprises a metal. The method comprises: performing a pre-cleaning of a surface of the substrate and a surface of the electrodes using a plasma or ozone to provide a precursor sensor; cleaning the precursor sensor to remove excess hydroxyl from the surface of the electrodes; and after removing excess hydroxyl from the surface of the electrodes, storing the sensor to decrease a surface energy of the substrate relative to a surface energy of the electrodes to provide an enhanced sensor surface, wherein the enhanced sensor surface promotes congregation of particles in a region between the electrodes.

The step of storing the sensor may comprise storing the sensor under vacuum or partial vacuum conditions, or in a vacuum desiccator.

According to a related aspect there is provided a method of detecting a target biological entity in a biofluid. The method may comprise introducing the biofluid to a suspension to provide a precursor mixture. The biofluid may comprise a plurality of target biological entities. The suspension may comprise a plurality of nanoparticles, wherein each of the plurality of nanoparticles is functionalized so that it is able to bind with the target biological entity to produce a bound nanoparticle-entity assembly. The method may further comprise treating the precursor mixture to separate the bound nanoparticle-entity assemblies from nanoparticles not comprised in one of the bound nanoparticle-entity assemblies to provide a treated precursor mixture.

Advantageously, by functionalising the nanoparticles themselves, the transport of the target entities and subsequent concentration around the sensing region may be efficiently facilitated. The nanoparticles may have a high affinity with the electrodes themselves, for example, if both the electrodes and nanoparticles are made of the same material, e.g. gold. Additionally, the use of nanoparticles allows an electric field to be applied which may more easily attract the nanoparticles bound to the entities, and concentrate them around the sensing electrode. Thus, there is provided an efficient method of sequestering and concentrating target entities, which may possess an advantageous sensitivity to detecting the presence of target entities.

In an alternative approach, the 'naked' nanoparticles not yet bound to a target entity may be sequestered or selectively removed from the mixture, such that only bound nanoparticles-entity assemblies remain. Here 'naked' is used to refer to a nanoparticle which is functionalized but not bound to a target. The suspension may be a liquid suspension containing heterogeneous species, including the nanoparticles. Furthermore, the nanoparticles may be conductive nanoparticles, for example, metallic or semi-metallic nanoparticles.

The suspension may generally be any composition in which the nanoparticles are suspended as a heterogeneous phase, including a colloid. For example, the suspension may comprise a colloid of nanoparticles, or a colloid suspension of nanoparticles. The suspension may generally comprise nanoparticles of any size, and is not restricted to nanoparticles of a certain scale/dimension. Generally, the suspension is a composition that is miscible with the biofluid. For example, the suspension may be substantially aqueous, and the biofluid may also be aqueous. Thus, the biofluid and suspension may be miscible for any ratio of volume of biofluid to suspension.

BRIEF DESCRIPTION OF THE FIGURES

These and other aspects of the invention will now be further described, by way of example only, with reference to the accompanying figures in which.

DETAILED DESCRIPTION

There are now described methods and systems for selectively detecting the presence of a target biological entity within a fluid medium, and methods of preparing a surface of a sensor for improving the detection of the presence of a target biological entity.

Figure 1:
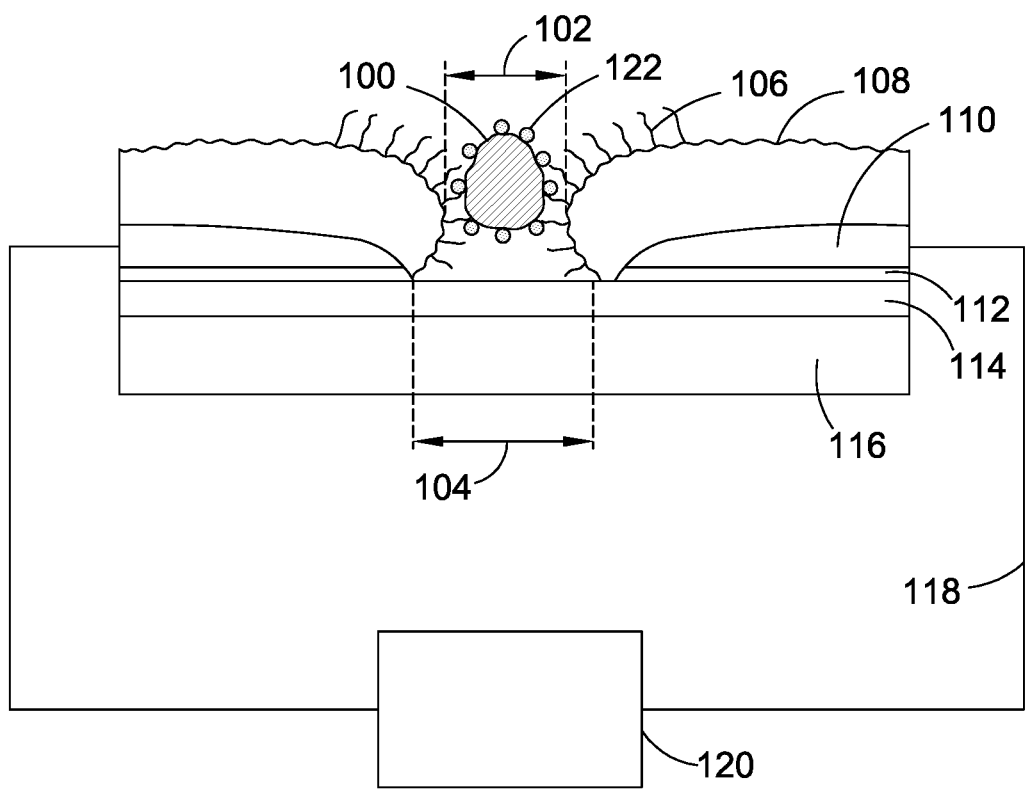
FIG. 1 shows the profile view of the electrode pair with a bound target biological entity.

FIG. 1 shows a system in which a biological entity 100 has been bound by target recognition molecules 106 between the pair of electrodes. The initial electrodes 110, 112 represent metallic or otherwise conductive materials which are disposed onto an insulating platform 114 which may comprise $SiO_2$. The lower layer 116 underneath the upper platform may comprise Si. The target recognition molecules may 106 be aptamers, which have been specifically chosen to only bind to the target biological entity 100. The target biological entity 100 may be a protein, or more specifically a vesicle such as an exosome 404. The distance 104 between the two electrodes 110 is 200 nm or less, or preferably 100 nm or less.

Between the electrodes 110 there may be provided a region which defines a sensing region. An example of this sensing region can be seen in FIG. 1. The distance 102 between the sensing regions of the two electrodes 110 is generally smaller than the lateral distance 104 between the initial electrodes.

The device is designed to detect a target biological entity 100 in a biofluid by measuring or detecting a change in current. Device 120 is at least able to apply a voltage or potential difference across the two electrodes 110 via the circuit 118. The voltage applied will generally be between −2V and 2 V. A different voltage may be predetermined based on characteristics (such as conductivity, permittivity, size, charge, or isoelectric point) of a specific target entity.

It will be appreciated by the skilled person that depending upon the implementation device 120 (or characterization of the sensing region) may not be limited to applying a constant steady voltage. Thus in some implementations, the device is able to apply a time-dependent potential difference resulting in either a variable direct current or even an alternating current. Implementations of the device are not limited to measuring merely a direct (or alternating) current. Thus in other implementations, which are still aimed towards detecting a target entity 100, the device 120 is able to measure any or a combination of: resistance, conductance, impedance, or even capacitance. For example impedance spectroscopy may be performed in order to characterize the sensing region e.g. distinguish a target molecule. This list is not exhaustive.

Figure 2:
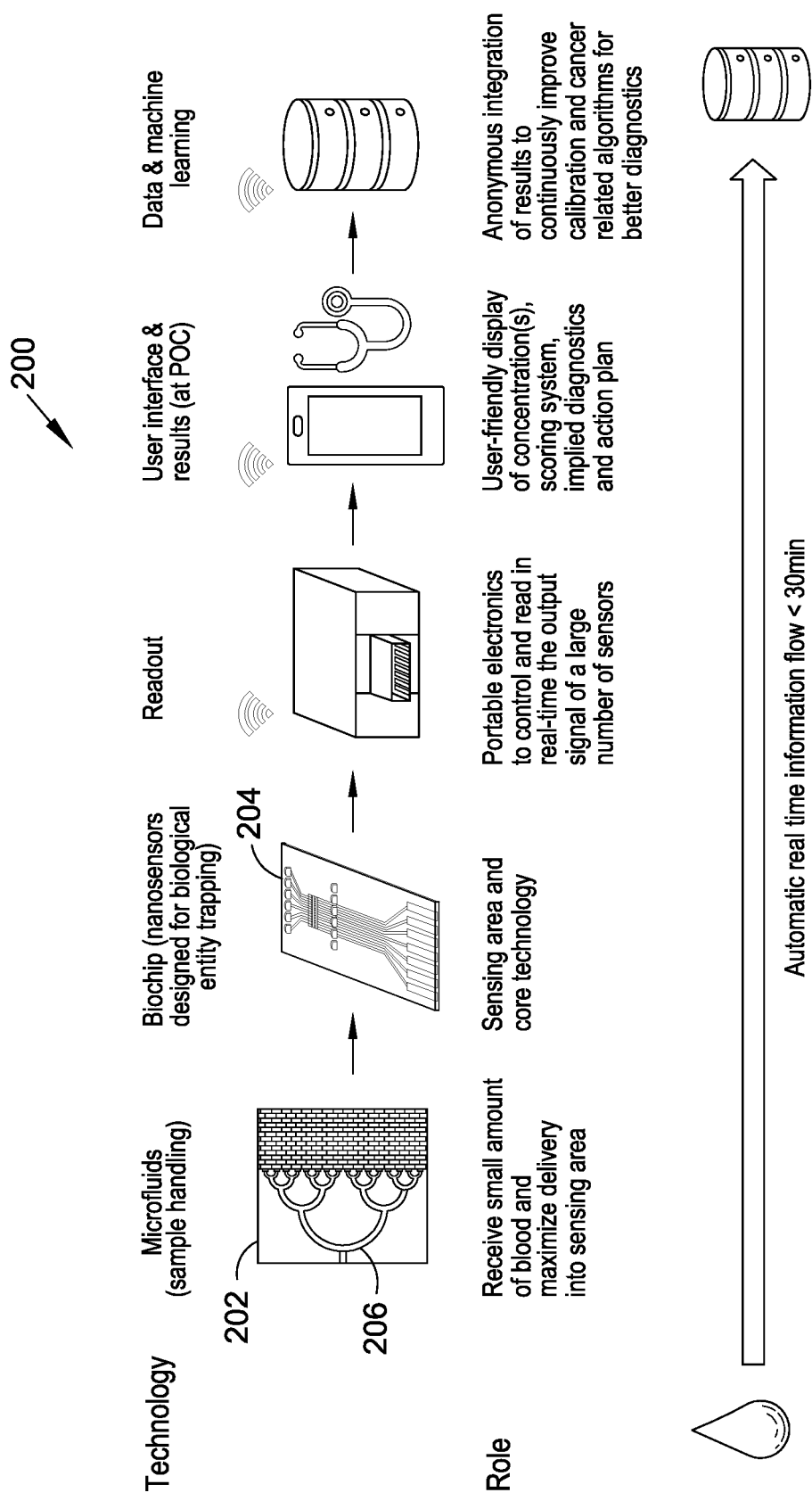
FIG. 2 shows a model microfluidics system and a general flowchart of a method for the detection of biological entities.
Figure 3:
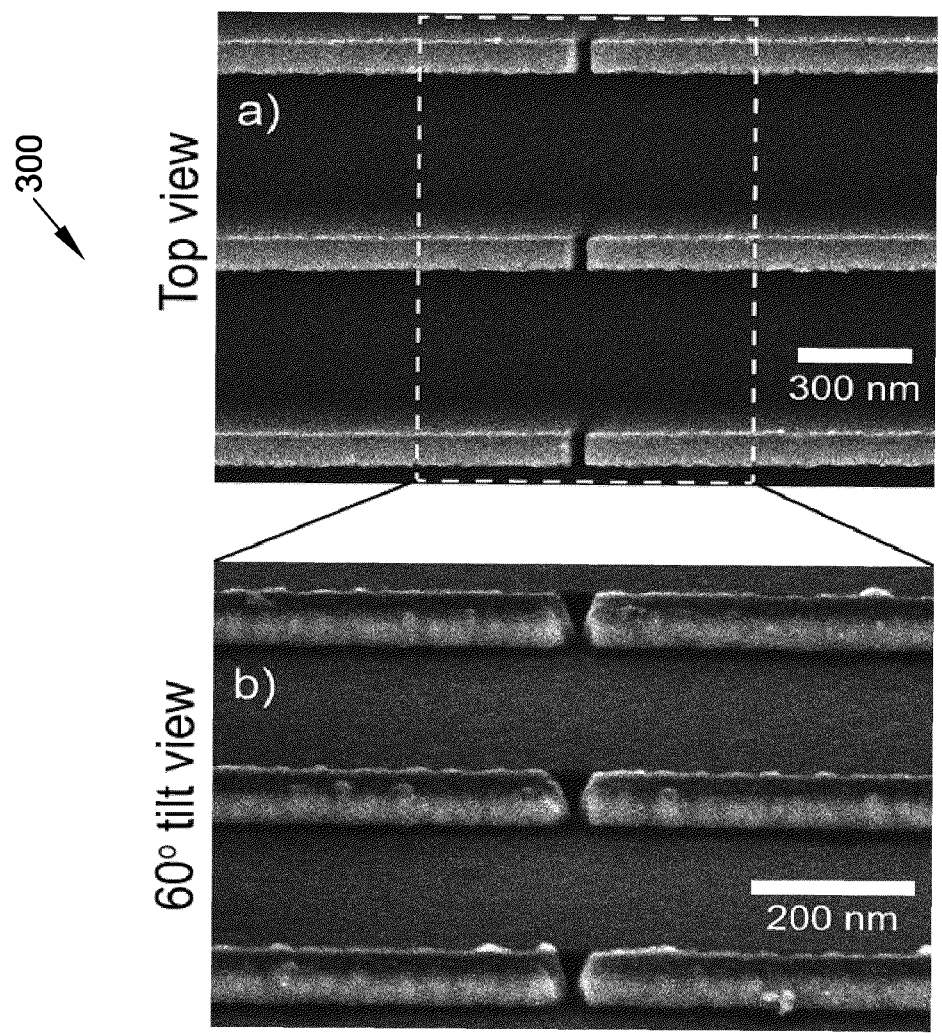
FIGS. 3a and 3b show, respectively, a plan view image of an array of electrode pairs, and a plan view image tilted 60 degrees of an array of electrode pairs.

FIG. 2 illustrates one example procedure 200 for the detection of biological entities, where a microfluidics chip 202 is employed to direct the flow of the biofluid. Advantageously, hundreds and preferably even hundreds of thousands of sensors comprising electrode pairs 110 may be disposed onto a sensing area 204 bearing, or adjacent to, such a microfluidics chip 202. In one implementation, a microfluidics chip such as 202 is able to separate and disperse the biofluid prior to being passed over the plurality of sensors. In this way, a very large surface area of sensing region 204 is able to be covered with only a small amount of biofluid. In another implementation of the microfluidics chip, the chip bears at least one channel 206 which guides the biofluid directly over an array of sensors in the first instance. For example, FIGS. 3a and 3b show three electrode pairs 300 disposed in parallel at two different visual perspectives.

Using microfluidics has the advantage, especially in the medical diagnostics industry, that only a small amount of liquid biopsy needs to be extracted (for example, 100 μL of fluid such as blood, as in FIG. 2). Furthermore, the device can be easily utilised in a point-of-care manner. The microfluidics and electrode sensor array may be mass-produced according to a predetermined and highly adaptable fabrication specification.

FIGS. 4a and 4b show an electrode pair in an un-bound 402 and bound 406 (with target entity 100) state, respectively. It is contemplated that more than one binding event 406 may occur at a single electrode-pair 110 sensor. Thus FIG. 4b, for example, shows an experimental setup after which multiple target entities 100 have been sequentially bound in-between an electrode pair.

Figure 4:
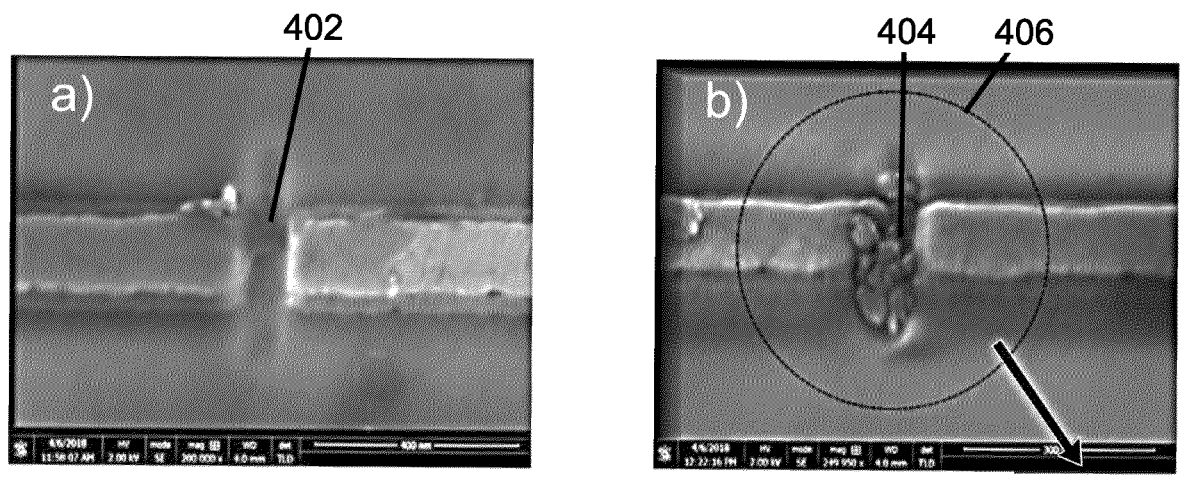
FIGS. 4a and 4b show, respectively, a plan view image of a single electrode pair, and a plan view image of an electrode pair in operation, comprising a group of bound exosomes coupled to magnetic nanoparticles for visualization by scanning electron microscopy.
Figure 5:
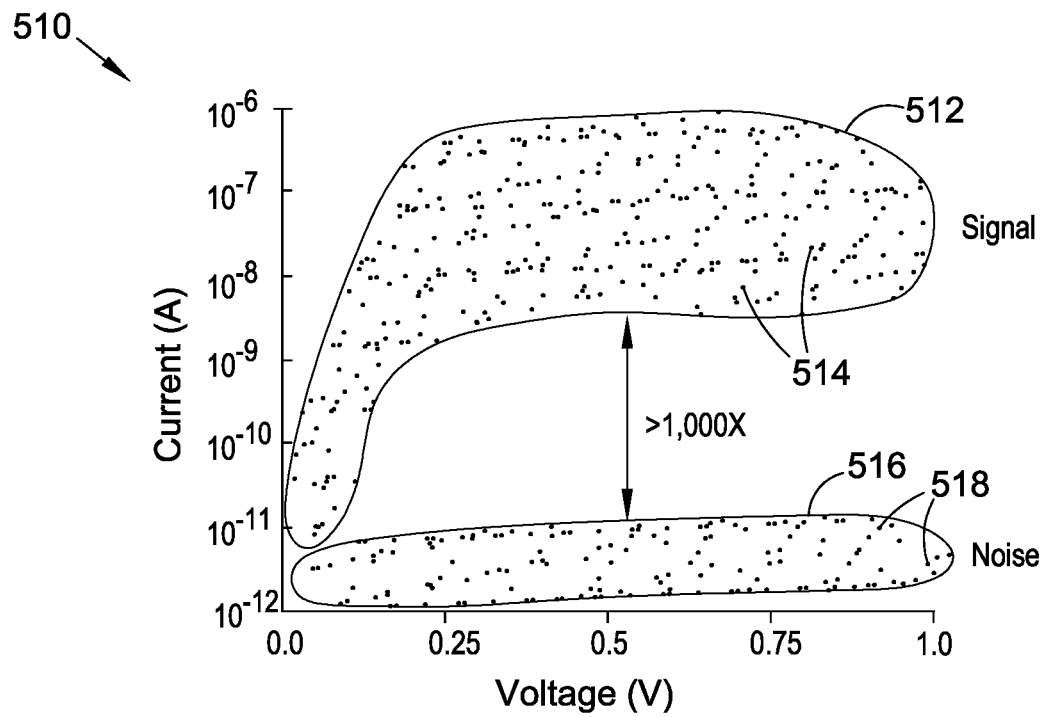
FIG. 5 shows a current vs. voltage graph, showing signals derived from aggregate bindings of exosomes (indicative of FIG. 4b) and non-binding events.

In some implementations, an increase in current may be detected, which may be indicative of a target entity. FIG. 5 shows a current/voltage graph 510 which plots a current signal where a binding of a target entity 100 (in this case exosomes) has occurred. The number of sensors utilised simultaneously in this scenario is roughly 100. FIG. 4 depicts an example in which the exosomes are suspended in a phosphate-buffered saline (PBS) solution with pH 7.4. This may be an example of a synthetic biofluid, or alternatively, the PBS may be used as an additive to a physiological biofluid with a similar pH. The various ionic salts dissolved within the PBS solution give it an improved conductivity. Therefore, when the Exosomes 404 become bound to the electrodes 110, the displacement of the PBS from between the sensing region may cause the conductivity in the region between the electrodes to decrease. In this way, the threshold for detecting the target entity may be predetermined to be a certain decrease in absolute current or relative current magnitude.

FIG. 5 shows, schematically, a current vs. voltage graph 510, showing signals derived from aggregate bindings of nanoparticles/exosomes and non-binding events. FIG. 5B relates to a system in which the exosomes are initially suspended in a phosphate-buffered saline (PBS) solution with pH 7.4.

The upper grouping of signals 512, with current range of about $10^{-6}$ to $10^{-8}$ Amps, corresponds to groups of individual measurements 514 where a successful binding event has occurred between the nanogap of the electrodes. In the context of these exemplary results and group 512, a binding event 514 corresponds to either an individual nanoparticle/exosome bridging the gap or an aggregate of nanoparticles/exosomes bridging the electrode gap. It will be appreciated that even the binding events 518 with low current values (i.e. less than $10^{-8}$ Amps, corresponding to fewer, or a single, nanoparticle/exosome bridging the electrode gap) still provide a signal a factor one thousand greater than a signal corresponding to a non-binding event 518. The lower group 516 of measurements corresponds to such non-binding events, for example, mere adsorption of targets onto a surface of an electrode, but where the gap 102 is not bridged.

Figure 6:
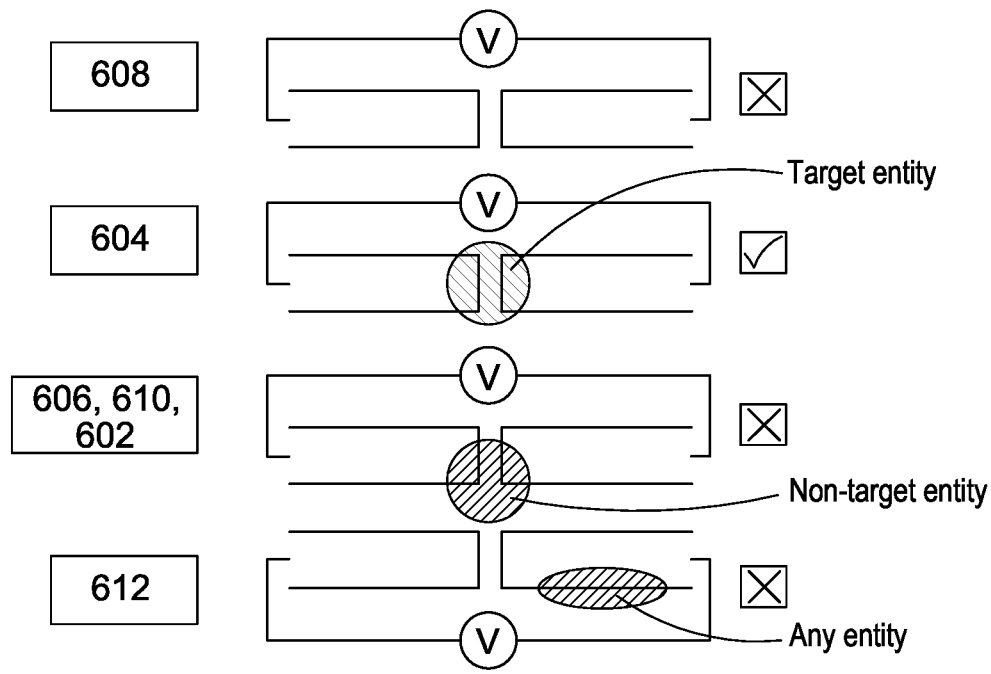
FIG. 6 shows a variety of potential binding/adsorption scenarios for target entities and non-target entities.

FIG. 6 illustrates a variety of successful binding events and non-binding events. Scenario 608 illustrates an electrode pair (which may have sensing aptamers attached) but no bound or adsorbed biological entity. Event 604 represents a successful binding event of the target entity between two aptamers/antibodies attached to each electrode of the electrode pair. Scenario 606 illustrates an electrode pair where a non-target entity is bound to the recognition molecules.

Scenario 610 illustrates an aggregate of various target and non-target entities or bio-complexes, which are not bound to the electrodes, but have become merely adsorbed onto the surface. Further, the aggregate binding is in contrast to the state where a dual, permanent, binding occurs of both a target entity and a non-target entity in parallel 602. In 602, both molecules are bound, and therefore possess lower dissociation constants. Event 612 represents merely adsorption of an entity onto a wall of an electrode, but which does not bridge the electrode gap. Therefore, no 'Ohmic' current representative of a resistor (or, a very low or indiscernible signal) will be generated due to event 612.

In some implementations, in place of a real liquid biopsy or biofluid being used, a synthetic biofluid may be used. This synthetic biofluid will contain the target entity, and may be used for the purposes of testing or calibrating the sensor device. For example, a range of synthetic fluids having various pH levels and a range of target entities with various pI values may be passed over the sensor in different combinations. The current response of the device for each combination will be measured. In this way, it may be possible to more accurately select an appropriate detection threshold for a particular combination of serum pH and target-entity pI.

In some implementations the device may comprise a substrate or chip having a lateral dimension of <1 mm, potentially <100 μm, <10 μm, or <1 μm, optionally in a microfluidics system. In some implementations the sensor comprises a pair of electrodes configured to detect a protein in a bodily fluid. The separation of the electrodes defines a gap having nanometre dimensions, which defines a sensing region, which may have a lateral separation of <50 nm, <20 nm, <10 nm, or in implementations ~5 nm or less e.g. ~2 nm.

Figure 7:
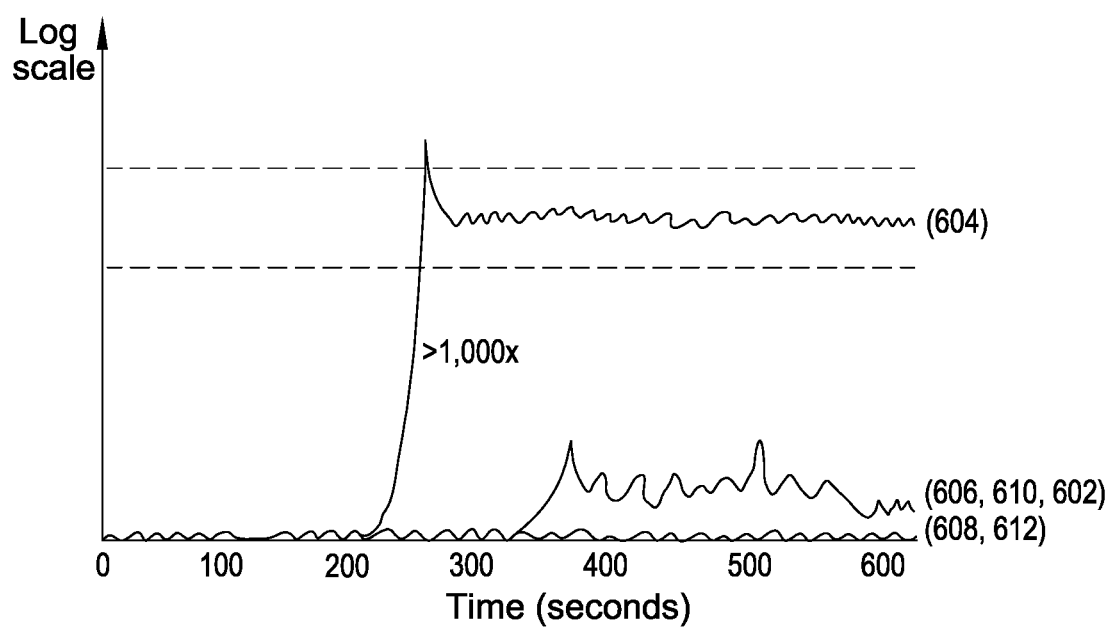
FIG. 7 shows a representative current-time graph illustrating binding/adsorption scenarios.

FIG. 7 shows, schematically, an example current-time graph illustrating various potential binding/adsorption scenarios. The upper signal 604 corresponds to the target entity binding event 604 in FIG. 6, corresponding to a single target entity bridging the electrode gap 102. Other non-target-binding events (606, 610, 602, 608, 612) cause a much lower signal, in implementations with a lower magnitude than the signal produced by a binding event by a factor of e.g. approximately 1000.

Further methods and corresponding systems for selectively detecting the presence of a target biological entity, such as a protein or extracellular vesicle, e.g. exosome, within a biofluid are described below.

Figure 8:
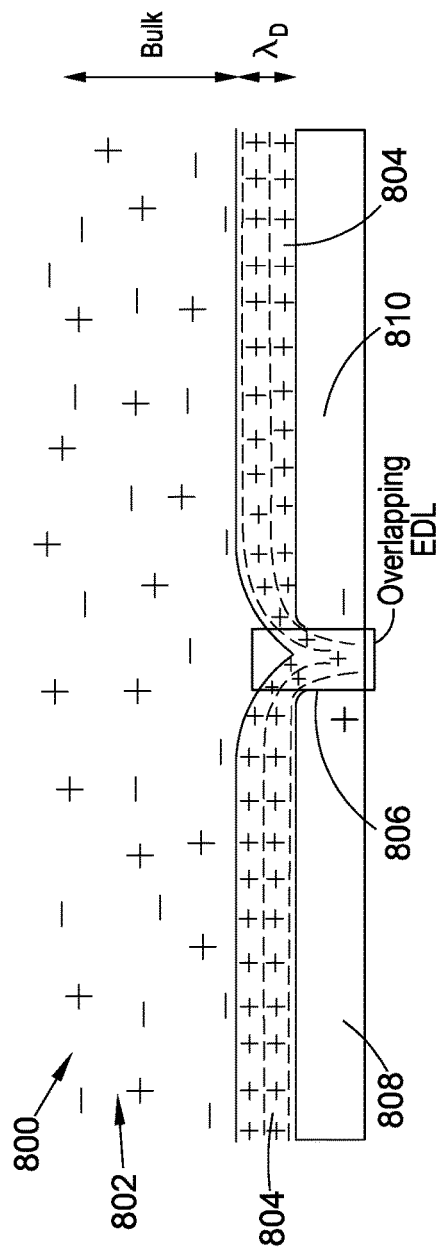
FIG. 8 illustrates a profile cross-sectional view of an electrode pair with a nanogap, and an electrical double layer in the surrounding fluid.

FIG. 8 illustrates a sectional view of an electrode pair with a nanogap, and an electrical double layer in the surrounding fluid. In this sensor example 800, individual ions 802 persist in the medium, and concentrate over the electrodes' 808, 810 surface to form a double-layer 804. This double layer can be seen to overlap in the sensing region between the electrodes 806.

Various other advantages may be associated with narrower gaps on the order of 20 nm, 10 nm, or even ~5 nm or ~2 nm, despite the difficulty associated with reproducibly fabricating such narrow electrode gaps. For example, other non-classical electron transport effects (in addition to tunnelling) may be encouraged, such as Flickering resonance. Generally, this mode of electron transport only occurs in the range of about 1-2 nm.

Entity Characterization with Alternating Electric Fields and Nanoparticles:

In some implementations, the sensors bearing electrode pairs, or array of sensors/electrodes, may not need to be functionalised with target recognition molecules (e.g. aptamers). For example, in some examples it is not necessary to rely on mass transport/diffusion in order for the target entity to reach the sensing region of the electrode. Alternating electric fields may be used to induce an electrophoretic force on conductive nanoparticles bound to target entities, and bound nanoparticle-entity assemblies may be actively transported to, and concentrated around, a sensing region or nanogap of an electrode.

Advantageously, dielectrophoresis (DEP) offers rapid concentration and isolation of nanoparticulate matter that does not depend on specific chemical binding or alterations. The DEP process commonly utilizes two electrodes in solution that are subjected to an alternating electric field (E-field). The force on the particles derives from the fact that the alternating electric field induces local dipoles within the particles. These local dipoles cause a net force toward, or away from, the E-field gradient depending on: the frequency of oscillation, and the relative dielectric permittivity of the particle and surrounding medium.

With regards to examples including dielectrophoresis in the present disclosure, and indeed with regards to the present disclosure in general, PCT application PCT/GB2019/051233 with publication No. WO/2019/211622 is hereby incorporated by reference.

Figure 9:
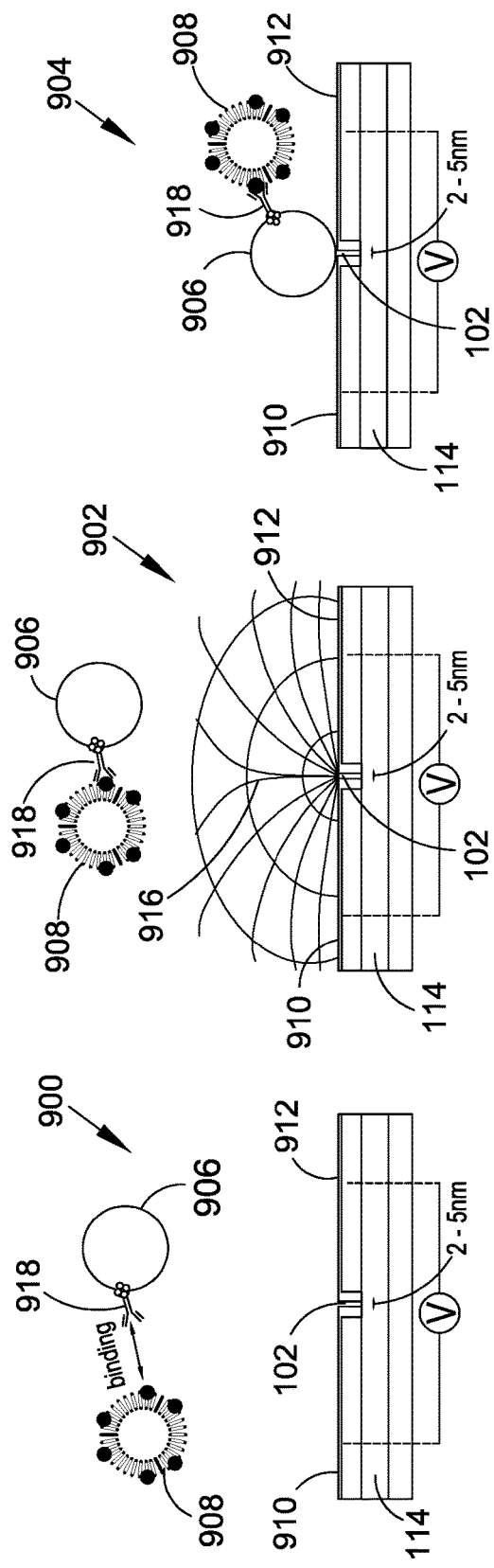
FIG. 9 illustrates a method of using Dielectrophoresis (DEP) and current measurements to capture and detect a target molecule using gold nanoparticles.

FIG. 9 illustrates an example of a method of using dielectrophoresis (DEP) to influence and accelerate the transport of nanoparticle-entity assemblies/pairs. FIG. 9 further illustrates the capture and characterization of the target entity 908 with the aid of gold nanoparticles 906. The electrode 910, 912 are gold in the illustrated example, wherein a nanogap of approximately 40-50 nm exists, although this may be as low as 10 nm or even 5 nm. The electrodes are provided on a substrate 14 as in other implementations.

Target entities such as exosomes 908 forming part of a biofluid may be sequestered by functionalised nanoparticles 906. In the example of FIG. 9, the nanoparticles 906 are gold nanoparticles. They are functionalised with an aptamer 918 or other suitable linker which interacts to bind with the exosome 908.

Step 900 shows such a binding/sequestering event taking place in order to form the nanoparticle-entity assembly. Sufficient time is allowed for the exosomes 908 to interact with the GNPs 906 and form a bond.

Step 902 depicts an electric field 916 being applied to the medium such that a force is exerted on the nanoparticle(s) 906. Since the nanoparticles are bound to the exosomes, the exosome also become attracted to the electrode sensing region. An alternating current should be applied to induce an alternating electric field. In some implementations a frequency of up to about 1.5 MHz may be used. Advantageously, the electrodes 910, 912 do not need to be functionalised with aptamers or any kind of target recognition molecule. Gold nanoparticles (GNPs) have a natural affinity, i.e. a thermodynamically favourable interaction, with gold electrodes.

Implementations of the described system/method have small gaps between the electrodes, e.g. less than ~10 nm, to facilitate bridging this gap with one or a few nanoparticles.

After the attraction and concentrating 902 of the nanoparticle-entity assemblies around the sensing region 102, the assemblies bridge the electrode nanogap 102. A direct current is generally then applied, which is used to characterise/measure a response of the sensing region in order to identify whether the assemblies (and thus exosomes) are present. Such a direct current may serve the further purpose of providing an activation energy to the bound nanoparticles to increase a connection between the at least one nanoparticle and at least one electrode, and/or a connection between adjacent nanoparticles. Without wishing to be bound by theory, an activation voltage, which causes an activation current, may effect Joule heating in the nanoparticles, causing a fusion between the metallic nanoparticles and electrodes.

A voltage of around 1 V may be applied to produce a direct current in 904. A baseline current (where no bridging occurs, e.g. as in FIG. 10A) may be around 1-20 pA. A current produce from a bridged gap (e.g. as in FIG. 11A, described below) may be around 1-100 nA. Thus, a signal to noise ratio of over a thousand may be achieved in implementations of the described method.

EXAMPLES

Figure 10A:
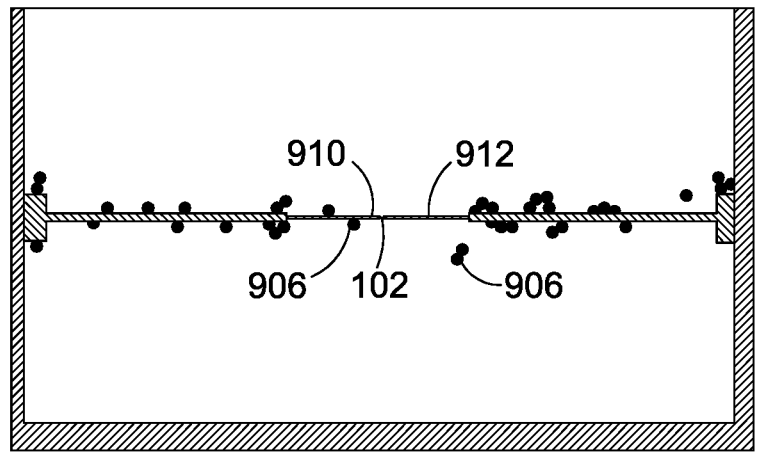
FIGS. 10a and 10b show, respectively, a plan view scanning electron microscope (SEM) image of a single electrode pair with nanogap, having single and aggregate gold nanoparticles adsorbed onto the electrodes, and a plan view scanning electron microscope (SEM) image of an array of five electrode pairs with a nanogap.

FIG. 10A shows a plan view scanning electron microscope (SEM) image of a single electrode pair with nanogap, having single and aggregate Gold nanoparticles adsorbed onto the electrodes.

The resultant structure shown in FIG. 10A was generated using the method described above in conjunction with FIG. 10A. However, no exosomes are present in the SEM image or method used in conjunction with FIG. 10A. The electrodes 910, 912 shown are un-passivated.

In detail, example experimental parameters are as follows:
A gap size of ~40-50 nm is used;
An electric field is generated with an AC amplitude of 1.5V, is equivalent to an RMS voltage (Vrms) of ~1.06V.
The frequency of the electric field is driven at 1 MHz, and held constant for 30 seconds.
PBS solution of 100× dilution is used;
Gold nanoparticles of stock concentration are used (2.6× $10^{10}$ per ml) are used;
The total volume of the resultant fluid is 45 μL
Control (i.e. no DEP applied) showed that no attraction occurred between GNPs and electrode.

Figure 10B:
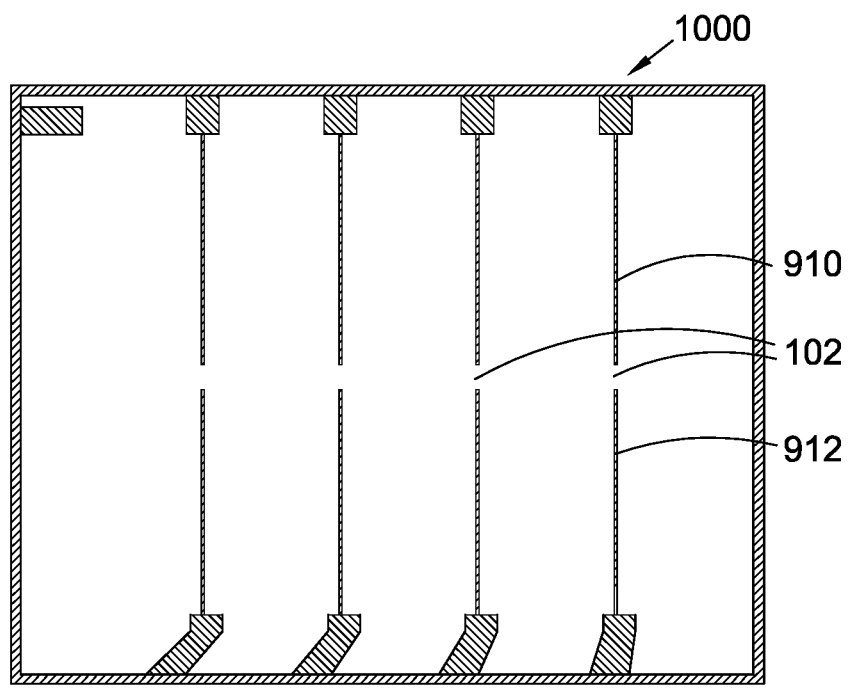

FIG. 10B shows a plan view scanning electron microscope (SEM) image of an array of five electrode pairs with a nanogap. Each of the sensing regions 102 shown is equivalent to the sensing region/nanogap in FIG. 10A. Again, each of the electrodes 910 and 912 are gold and grown such that each end approaches the other in order to produce a nanogap of less than 200 nm, or even less 100 nm. An array 1000 of sensors as shown here may comprise far more than 5 electrode pairs. For example, more than 10 or 100 sensors may be used, for example as used to produce the results in FIG. 5B.

When used, for example a method to attract and characterise nanoparticle-entity assemblies as in FIG. 9, each of the sensing regions 102 may be used to apply an alternating electric field, and subsequently attract/concentrate assemblies. Each sensing region 102 may then be used to apply a direct current to characterise a response of each of the regions to identify the presence of target entities.

Figure 11A:
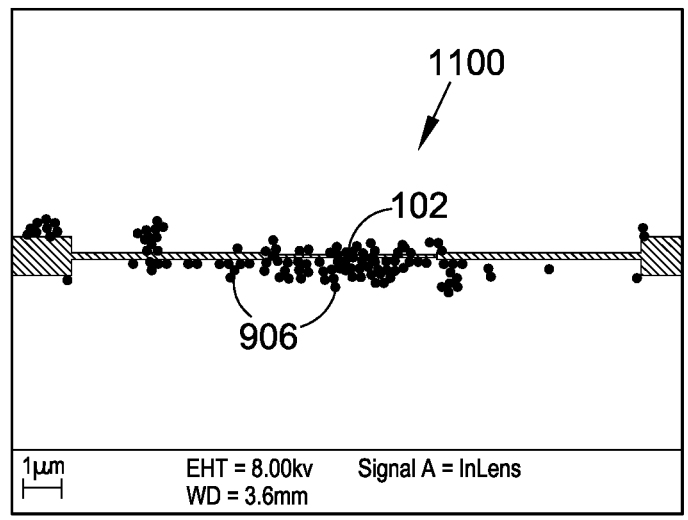
FIGS. 11a-11c show, respectively, a plan view scanning electron microscope (SEM) image of a single electrode pair with nanogap, having gold nanoparticles bridging the nanogap between the electrodes, a higher resolution image of the region around the nanogap in FIG. 11a, and voltage current plots of a response of the bridged nanogap in 11a and 11b (left-hand side) and a response of a non-bridged nanogap.

FIG. 11A shows a plan view scanning electron microscope (SEM) image 1100 of a single electrode pair with nanogap 102, having gold nanoparticles 906 bridging the nanogap between the electrodes. The nanogap 102 in FIG. 11A shown is approximately 40-50 nm. The conditions for providing an alternating electric field to the medium to concentrate the GNPs 906 using DEP are: 1.5 V amplitude AC at a frequency of 1 MHz; PBS used at 1% dilution; DEP conditions were sustained for 1 minute.

Figure 11B:
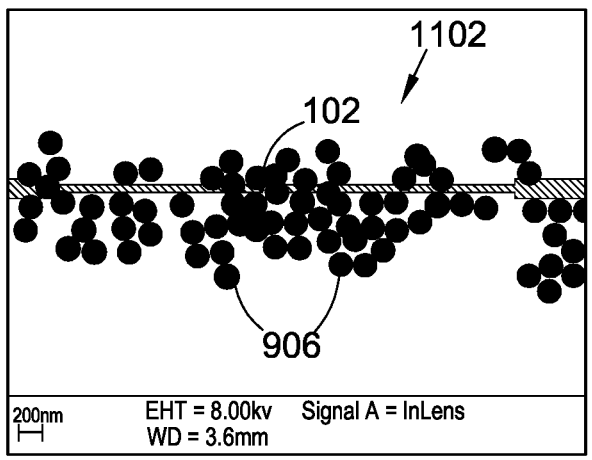
Figure 11C:
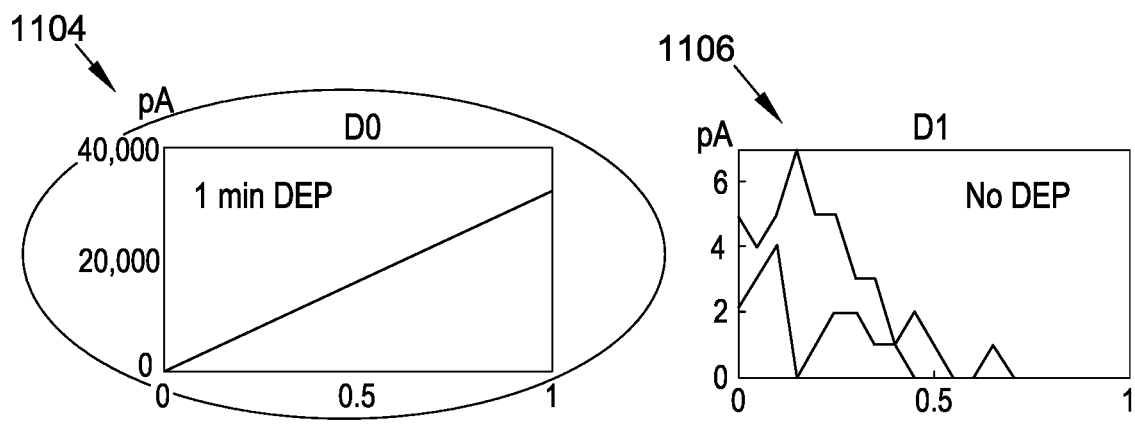

It should be appreciated that, in the examples, no bound nanoparticle-assemblies have been created prior to DEP and characterization. FIGS. 11A-11C merely show an example with 'naked' unbound gold nanoparticles. However, the skilled person will appreciate that results described here may be equivalent to a result where bound nanoparticle-entity (e.g. nanoparticle-exosome) assemblies are used. Thus, these results relate to an example where no filtering step has been provided to remove the naked/unbound GNPs.

FIG. 11B shows a higher resolution image 1102 of the region around the nanogap in FIG. 11A. It can be seen that the GNPs 906 form a contiguous bridge between each end of the electrode either side of the nanogap 102. Thus, a conductive path is formed which may behave as a resistor, and thus can be characterised by either applying a DC or AV voltage of approximately 1-1.5 V.

FIG. 11C shows voltage current plots of a response 1104 of the bridged nanogap in 11A and 11B (left-hand side) and a response 1106 of a non-bridged nanogap. During application of a DC voltage used to characterise a response of the sensing region (to identify presence of the GNPs bridging the nanogap), a signal of 33 nA was recorded. This relates to a signal to noise ratio of over 10,000.

The derivation of this signal-to-noise ratio can be appreciated from the current-voltage plots 1104 and 1106. The current-voltage profile in 1104 is linear, and thus represents an 'Ohmic' response representative of a classical resistor, corresponding to the structure of FIGS. 11A and 11B. In this sense, the bridged gap seen in FIG. 11B behaves as a classical resistor. The signal in 1106 shows no Ohmic response whatsoever, as it corresponds to a nanogap which is not bridged by any GNPs. Thus, graph 1106 corresponds e.g. to FIG. 10A, where adsorption of the GNPs has occurred on the surfaces of the electrodes away from the sensing region 102.

FIG. 11C is thus an example of characterising data 1104, 1106 produced from a sensing region when a direct current is applied between the electrodes. This further demonstrates the characterizing of a response of the sensing region to the nanoparticle sensing voltage to determine treated precursor mixture characterizing data. For example, characterization methods (for example, including pattern recognition methods, which may be learned by a machine) may be used to characterise 1104 as data representative of a bridged gap, or the presence of the target entity. Data 1106 is an example of data which may be characterized as an absence of a target biological entity.

Activation of Sensor:

As described above, the bound assemblies containing nanoparticles, which may be e.g. gold nanoparticles (GNPs) or other suitable metal and/or conductive nanoparticles, form a contiguous bridge between opposing electrodes of the Nanogap 102, as exemplified in FIGS. 11A and 11B. This bridging forms a conductive pathway, thus allowing detection of nanoparticles by applying a DC or AV sensing voltage of approximately 1-1.5 V.

However, we disclose herein a method of further conditioning the sensor (having an electrode gap bridged by nanoparticles) to significantly improve the sensitivity of detection of the bridged Nanogap, comprising applying an activation voltage to the bridged gap.

By applying an activation voltage, a 'liquid-solid phase' may be achieved within the bridged/trapped nanoparticle(s) between the Nanogap electrodes. Consequently, the liquid-solid phase allows a redistribution of surface atoms of the nanoparticles away from the bulk crystalline structure. The surface atoms may therefore diffuse onto the nanoparticle-electrodes interface. This phenomenon, caused by the application of an activation voltage, is surface diffusion.

Consequently, the activation voltage causes the nanoparticles to partially fuse/embed into the surface of the Nanogap electrodes, creating a wire-like connection. It has subsequently been identified that providing this activation causes a great increase in the sensitivity during the step of characterizing a response of the sensing region (i.e. the bridged Nanogap) when a nanoparticle sensing voltage is applied.

The activation voltage may also be viewed as an application of a nanoparticle restructuring voltage applied between the electrodes. Further alternative terminology for the formation of a wire-like structure is NP-electrode interface coalescence. Alternatively, in the scenario where multiple nanoparticles bridge the Nanogap electrodes, the phenomenon may be referred to as 'coalescence', where two or more nanoparticles become fused together.

In practice, a voltage of around 5V is applied across the bridged Nanogap to cause the NP surface diffusion/activation. Advantageously, however, this voltage is much lower than would be necessary to cause nanoparticles to fully enter a liquid state (i.e. exceed their melting point). Thus, activation at relatively low voltage is possible because this redistribution of nanoparticle surface atoms occurs at a temperature far below the melting point of the bulk material. For example, concerning gold nanoparticles (GNPs), the melting point for bulk gold is 1,337 degrees kelvin.

After the activation voltage has been applied, the circuit resistance across the bridge Nanogap falls sharply by an order of magnitude of around $10^6$, i.e. from a range of G$\Omega$ to k$\Omega$. Thus is due to the increased conductivity resulting from the wire-like connection of the fused nanoparticles.

In general, the activation voltage step allows for an enhanced current measurement during the sensing stage of the process (i.e. to detect the presence of target particle, and an improved signal-to-noise ratio. Furthermore, as a result of this increased sensitivity, and the more robust nature of the fused wire formed by activation, the likelihood of a false negative is dramatically reduced (including to a likelihood of zero) given the enhanced sensitivity of the post-activation structure.

Figure 12:
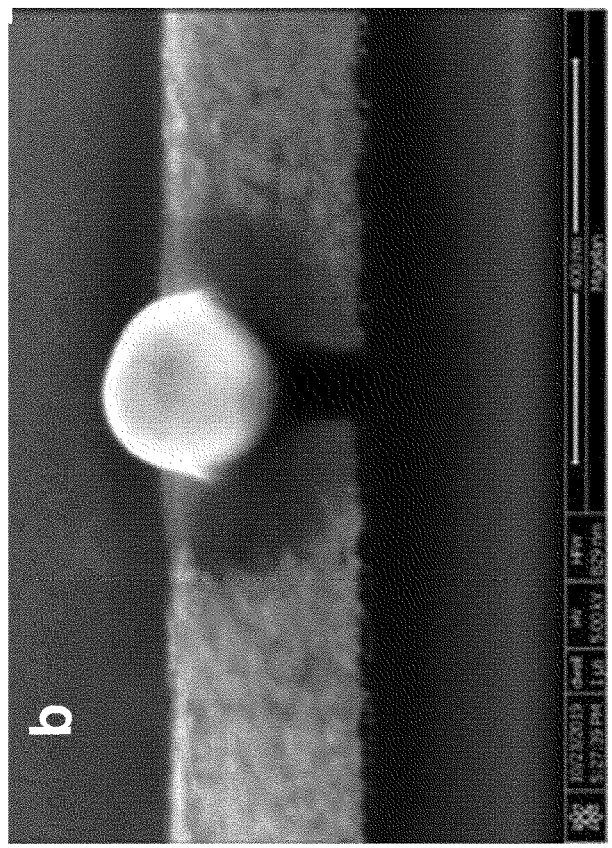
FIGS. 12a-12b show, respectively, a scanning electron microscope image of an electrode pair bridged by an adsorbed gold nanoparticle, and the same electrode pair and nanoparticles after an activation voltage has been applied to fuse the nanoparticle and electrode surfaces.
Figure 12:
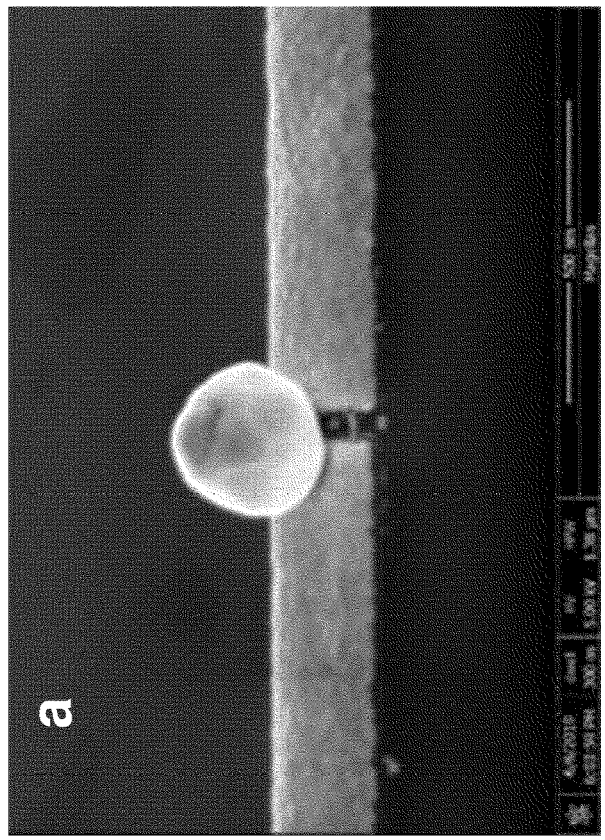

Example Activation Strategy: FIG. 12a show a scanning electron microscope image of an electrode pair bridged by an adsorbed gold nanoparticle. FIG. 12b shows the same electrode pair and nanoparticle after an activation voltage has been applied, causing the nanoparticles to partially fuse to the surfaces of each electrode of the electrode pair. However, it will be appreciated that FIG. 12 merely exemplifies the fusion which may occur between nanoparticles and electrodes upon application of an activation voltage (e.g. which may be DC).

The nanoparticle shown in Figures is absent a functionalisation, and is absent a bound target entity. In implementations, nevertheless, the nanoparticle may be bound as part of a bound nanoparticle-entity assembly, where the nanoparticle still bridges the gap of the electrode to form a link. Alternatively multiple nanoparticles (each part of a bound nanoparticle-entity assembly) may bridge the gap between the electrodes to form a chain. Thus, upon application of an activation voltage, the one or more nanoparticles forming a link or chain between the gap may coalesce with one another. Further, the point of contact between respective nanoparticle and electrode surfaces may fuse. Both of these effects result in an increased degree of connection between the electrodes. In other words, the fused link/chain has improved conductivity relative to the conductivity of a nanoparticle which is only seated (i.e. not fused) between the electrode gap.

The activation may be achieved by providing constant (DC) voltage of 5 V for a period of 3 seconds in dry conditions. This is for gold electrodes separated by 50 nm, and having a width of 300 nm, where the gold electrodes are bridges by nanoparticles with a diameter of 100 nm, or 200 nm, for example. As a result of the activation, the subsequent resistance measured across the electrodes reduces to e.g. around 2.5 K ohms (from around the order of G ohms before), with relatively small standard deviation. Generally, the decrease in resistance may be one, two, three, or even more (e.g. six) order(s) of magnitude.

Moreover, activation may cause the functionalised surface of the nanoparticle to become destroyed, thus resulting what is effectively a 'naked' nanoparticle, which has an improved electrical connection with the electrodes (e.g., by an order of magnitude of around two). In a specific example, GNPs are functionalized with Neutravidin, which present a lower conductivity (when bridging the electrode pair gap) than naked GNPs by around two orders of magnitude. Beneficially, once the nanoparticles (i.e., the bound nanoparticle-entity assemblies) are in the gap the nanoparticles can be conditioned/activated, such that the conductivity increases by two orders of magnitude. It is believed that this is due to the fact that the gold diffuses over the Neutravidin so that there is a cleaner electrode-metal-electrode connection, as opposed to a less conductive electrode-neutravidin-metal-neutravidin-electrode connection (it will be understood that Neutravidin is merely an example—other aptamers or functional linking elements may be used).

Furthermore, in order to ensure a secure seating or contact between a nanoparticle and the electrode prior to activation, a electrophoretic force (DEP) may be used to direct nanoparticles to the sensing region/electrode gap. As described in detail above, DEP can offers rapid concentration and isolation of nanoparticles, independent of specific chemical binding capability of the NPs. The DEP may be effected by two electrodes in solution through which is applied an alternating electric field (E-field).

Further to this, it is believed that high momentum created by DEP (compared to normal incubation) on nanoparticles can be used to accelerate NPs towards the electrode gap, thus enhancing the quality of the interface between the nanoparticle and electrodes. In other words, the presence of NPs may be more easily sensed (i.e., the sensitivity of the device is improved) due to an improved reliability by which nanoparticles are attracted to the sensing region (nanogap).

Furthermore, DEP allows very precisely positioning of the nanoparticle in the middle of the nanogap, in a way that it creates preferable or indeed ideal conditions for its sensing. An incubation approach via sedimentation (i.e., a passive approach absent the attractive forces provided by DEP) is less likely to provide a suitable nanoparticle-electrodes interface sufficient for sensing. The improvement in precisely and reliably positioning nanoparticles in the centre of the nanogap (i.e. as shown in FIG. 12a) also applies to bound nanoparticle-target assemblies, and/or nanoparticles functionalized with biomolecules.

electrodes surfaces. This in turn results in enhanced attraction/affinity (of nanoparticles), and an enhanced level of activation (e.g., upon providing an activation voltage, as described above)

The following table itemises an example set of preparation steps. The contact angles were measured at standard room temperature conditions, using 5 μL of ultra-pure water.

| | $SiO_2$ | | | Au | | | |
|---|---|---|---|---|---|---|---|
| Step | Contact Angle | Oxide level | Debris | Contact angle | Oxide level | Debris | Methodology |
| Initial | 90° | High | Yes | 90° | Medium | Yes | Storage in desiccator after photoresist removal |
| $O_2$ plasma | 25° | High | No | 25° | High | No | 1 min, 50% |
| Ethanol | 40° | High | No | 90° | Low | No | 20 min, 99% Ethanol |
| HMDS | 90° | High | No | 90° | Low | No | 4 mL, 150° C., 1 min active vacuum, 4 min passive vacuum |
| Ideal Target | 90° | High | None | 50° | Low | None | |

Nanogap Electrode Surface Preparation:

Prior to carrying out the activation and/or sensing method, we wherein disclose an additional preparation method, to obtain attractive forces being induced over the electrodes resulting in enhanced nanoparticle attraction and activation.

It is known that particles may accumulate at a gas-liquid or solid-liquid interface, for example to minimize surface tension in the suspending liquid. Linked to this is the concept of surface energy. The lower the surface energy of a given solid surface, the harder it is for a liquid to wet said surface.

For dilute suspensions with low particle concentrations, however, the trends are different for various fluids and/or particles. This is likely because for such dilute suspensions, the distance between particles are much larger than the particle size, thus the forces and the interactions between particles at/near the gas-liquid interface have less impact on the surface energy of the fluid.

For a surface having a low surface energy (i.e. a hydrophobic surface) surrounded by a suspension, the surface tension of the liquid increases, which promotes particles in the suspension to accumulate at the solid-liquid interfaces. Conversely, a higher surface energy can provide a surface with a greater affinity for adhesion or bonding with particles.

An integrated circuit-based chip usually comprises surfaces made of different materials with colocalized surface energies. For instance, substrates (e.g. comprising passivating oxides such as $SiO_2$) and active components (e.g. metals such as gold) may be used. Gold electrodes active surfaces have a lower surface energy than the substrate $SiO_2$ oxides.

According to the above, we disclose herein a surface treatment regime that advantageously balances the surface energy of two different materials, i.e. of the metal electrode surface and the substrate surface (which may comprise gold and $SiO_2$, respectively). The treatment enhances the wettability of the metallic electrodes over that of the $SiO_2$ when a liquid containing nanoparticles is introduced. This treatment thus promotes an accumulation of particles (including any unwanted contaminants) over the metallic electrodes, and discourages accumulation of particles around the substrate. This advantageously results in the creation of cleaner In more detail, the method includes a step of surface cleaning with a plasma, for example $O_2$ plasma. Merely by way of example, when $O_2$ plasma is used, it is exposed to the sensor surface, for example, for no more than around 1 minute to remove impurities. This process increases the surface energy of the metallic and oxide surfaces. However, the plasma clean (which may be $O_2$ plasma) or UV-ozone clean also produces or increases the state of oxides (i.e. hydroxyls) at the gold or $SiO_2$ surfaces, respectively. For example, the Si and electrode surface may become coated with OH functional groups.

Therefore, it is desirable to remove unwanted hydroxyls from the surface of the metal electrode (which would otherwise inhibit the adhesion/affinity with the nanoparticles). Thus, a further treatment step uses ethanolic solutions, for example 99% ethanol for no more than 20 minutes, to remove the oxides formed at the metallic (e.g. gold) electrode surface.

However, treatment with ethanol does not recover the Si substrate back to its previous state (having no residual oxide on its surface), and thus the $SiO_2$ surface remains highly oxidized. This is due to the fact that Si—O bonds are strong, durable and relatively chemically inert. Ethanol cannot readily remove such a Si—O bond.

However, certain agents or treatments can be used to further functionalise the hydroxyls present on a Si surface, for example hexamethyldisilazane, HMDS (also known as Bis(trimethylsilyl)amine). Siloxane links are readily formed with organosilicon compounds. Thus, HMDS reacts with the oxide surface of the Si substrate, forming a new coating (or layer) on the Si surface containing Siloxane (Si—O—Si) links, which have exposed organosilanes $Si(CH_3)_3$. These surfaces (i.e. the coating having exposed organosilanes $Si(CH_3)_3$) are highly hydrophobic, and are thus difficult to wet as they provide low surface energy. Advantageously, therefore, because the gold electrodes have been made free of oxides in the previous step (ethanol treatment), HMDS does not react with the electrode surface, and the surface energy of the electrode remains high (relative to the Si substrate surface). Therefore, forces that are more attractive may be established over the electrode surface than over the (coated) $SiO_2$ substrate.

Without the HMDS step or another treatment step to increase silicon hydrophobicity, the $O_2$ plasma could not be used in the treatment, because of the hydroxyl groups (being polar themselves, and having a high affinity with water) which form over the Si would result in high surface energy, causing undesirable and indiscriminate nanoparticle adsorption onto the substrate. Beneficially, the use of both plasma (e.g., an $O_2$ plasma) or UV-Ozone and HMDS provides an electrode surface having a surface energy which is much higher relative to the surface energy of the Si substrate (coated with $Si(CH_3)_3$). This difference in surface energy promotes nanoparticle congregation/adsorption/adhesion at the electrode surface only.

The result of the treatment provides two advantageous effects which ultimately lead to a device with improved sensitivity:

Firstly, the treatment produces an electrode surface with a low hydrophobicity (or high surface energy) relative to the hydrophobicity (or surface energy energy) of the substrate, which promotes the congregation of nanoparticles around the electrode surface. Specifically, the use of a functionalising agent (e.g., HMDS) to react with the oxide on the substrate to form a hydrophobic coating increases the surface energy of the electrodes relative to the $SiO_2$ substrate. This promotes to the accumulation of nanoparticles around the electrode gap/sensing region, caused by an increase in the surface tension of the liquid in a region around the substrate/electrode boundary. Furthermore, the treatment results in an enhanced attraction between the electrode's metal surface (e.g. gold) and the nanoparticles (which may also comprise gold, or consist of gold NPs), since higher surface energy makes a surface easier to adhere or bond to.

Secondly, the plasma or UV-ozone cleaning process removes impurities from the electrode surface, which results in a more reliable and effective activation during application of the activation voltage as described above. Specifically, by virtue of the plasma or UV-ozone cleaning step, the extent of nanoparticle "fusion" with the electrodes is increased, due to fewer impurities present on the metal electrode surface.

Generally, the purpose of the HMDS treatment is to decrease the surface energy of the substrate after treatment with the $O_2$ plasma. As an alternative to HMDS, it is possible to store the sensor for a period of time. The sensors should be stored for a period of a few days to obtain a preferable degree of hydrophobicity on the substrate, e.g. preferably around 3 days. The storage promotes the silicon surface to regain its original (i.e., prior to $O_2$ plasma treatment) level of surface energy, e.g., having a higher degree of hydrophobicity. It will be understood that storage comprises allowing the sensors to stand or rest for a period of time.

Optionally, the storage can take place under vacuum conditions (e.g., under at least a partial vacuum, such as a pressure of 0.5 bar or lower). The addition of vacuum conditions may help to prevent further oxidation and/or degradation of the substrate and/or electrodes. It will nevertheless be appreciated that storage under standard pressure and temperature conditions (i.e., 1 atmosphere of pressure) still results in the recovery of surface energy of the silicon substrate.

In one example, after storage for a period of 3.5 days, it is observed that the contact angle of the substrate with water (as above, with ~5 µL of ultra-pure water) returned to 90°. Therefore, the storage decreases the surface energy of the substrate to a comparable degree to the HMDS treatment.

Generally, the surface energy of the silicon substrate may be reduced with no HMDS (or other similar functionalisation agent suitable for functionalising hydroxyl groups with a hydrophobic functional group such as trimethylsilyl).

Advantageously, the storage, or vacuum storage, alternative to using HMDS allows a more scalable approach to decreasing the surface energy of the substrate, as an array of sensors can readily be stored simultaneously under standard pressure or vacuum conditions. Furthermore, it is observed that storage for a period of time provides a more reliable method of reducing surface energy on the silicon substrate. Thus, storage of sensors is reproducible such that less variation in surface energy between sensors prepared in this way is observed.

The storage or vacuum storage is generally an alternate to treating the substrate with HMDS following the $O_2$ plasma clean, however, it will be appreciated that HMDS may still be combined with storage or vacuum storage, in some examples.

A specific example conditioning strategy employing the storage treatment is as follows:
i. clean with $O_2$ plasma for around 1 minute;
ii. treatment with a 99% ethanol solution for around 20 minutes;
iii. rinse with isopropyl alcohol (IPA) and ultra-pure water (e.g., milli-Q water);
iv. storage for between 3 and 5 days (optionally under vacuum or partial vacuum, e.g., around 0.5 bar);
v. rinse with acetone;
vi. rinse with ethanol;
vii. rinse with IPA and ultra-pure water.

It will be appreciated that step iv) promotes recovery of the hydrophobicity of the silicon substrate surface.

Consistent with the above, it is also beneficial (e.g. for the sensitivity of detection of an array of sensors) to condition the electrodes by applying some form of activation energy (e.g., an activation voltage, or heat) to the electrodes or array of electrodes to perform the function of increasing a connection between the one or more nanoparticle assembled at the gap between each electrode pair. The activation energy could be provided by application of a voltage between each electrode pair to cause the nanoparticle(s) to improve an electrical connection to one or both of the electrodes, and/or to improve the connection between adjacent nanoparticles where a plurality of nanoparticles bridge the electrode nanogap. Without wishing to be bound by theory, it appears that a consequent current may cause localized Joule heating to achieve this. In another approach, the activation energy, and the resultant improvement in electrical connection as described above, may be provided by direct heating of the electrode or electrode array by e.g. an infrared lamp, oven, and other means configured to apply heat.

For example, the activation energy may cause the nanoparticles in the gap to fuse. Advantageously, the combination of preparing the sensor surface according to one of the above preparation methods, and the conditioning/activation step, yields sensors with an improved sensitivity of detection. In summary, the preparation step of storing the sensors increases the overall yield of working sensors, in an array of sensors, that will produce a detectable signal. In some examples, it may be preferable to store sensors for a period of around at least three days. In yet further examples, it may be preferable to store the sensors under vacuum or partial vacuum, and/or moisture-free environments such as storage in a vacuum desiccator.

In detail, the preparation steps to reduce the surface energy of the substrate cause a relative increase in the amount of particles that congregate around the nanogap of the electrodes. When an array of electrodes is used (e.g., as seen in FIG. 10B), the probability that each electrode pair of the array has an abundance of nanoparticles assembled at the nanogap increases. The activation of each electrode subsequently ensures that the congregations of nanoparticles become more securely connected to the electrode pair. Consequently, the probability that all electrode pairs will detect the presence of the nanoparticles is increased.

It is further observed that the storage period reduces a likelihood that nanoparticles will assemble on the silicon substrate surface. It is thus observed that nanoparticles are more likely to congregate in between the electrode nanogap following a preparation as described above.

The above embodiments have been described by way of example only, and are to be considered in all respects only as illustrative and not restrictive. It will be appreciated that variations of the described embodiments may be made without departing from the scope of the invention.

It should further be noted that the scope of the disclosure is not limited to the particular combinations described therein, but instead extends to encompass any combination of features herein disclosed.

The invention claimed is:

1. A method of detecting a target biological entity in a biofluid using a sensor, wherein the biofluid comprises a plurality of the target biological entities and nanoparticles, the sensor comprising a substrate bearing a pair of electrodes having an affinity with the nanoparticles, and wherein a region between the electrodes defines a sensing region, the method comprising:
 treating the biofluid with a suspension comprising a plurality of nanoparticles to obtain a treated mixture comprising bound nanoparticle-entity assemblies;
 introducing the treated mixture to the sensor;
 conditioning the sensor in the presence of the treated mixture by applying an activation voltage between the electrodes to increase a degree of connection between a surface of the pair of electrodes and bound nanoparticle-entity assemblies in contact with the surface of the pair of electrodes, wherein the conditioning comprises applying an activation voltage sufficient to fuse the bound nanoparticle-entity assemblies into a link or chain of two or more of the bound nanoparticle-entity assemblies linking the pair of electrodes; and
 detecting the presence of target biological entities by characterising the treated mixture, the characterising comprising:
  applying a nanoparticle sensing voltage between the pair of electrodes to detect a current through the two or more of the bound nanoparticle-entity assemblies linking the pair of electrodes, wherein the nanoparticle sensing voltage is less than the activation voltage;
  characterising a response of the sensing region to the nanoparticle sensing voltage to determine treated mixture characterizing data; and
 detecting the presence of the target biological entity from the treated mixture characterizing data; and
 wherein the pair of electrodes is separated by a lateral distance of less than 200 nm.

2. A method as claimed in claim 1, wherein introducing the treated mixture to the sensor further comprises: applying an electric field to the treated mixture to concentrate the bound nanoparticle-entity assemblies in the sensing region.

3. The method as claimed in claim 2, wherein applying the electric field induces an attractive force acting between the sensing region of the electrodes and the nanoparticle of the bound nanoparticle-entity assemblies.

4. The method as claimed in claim 2, wherein applying the electric field to the treated mixture comprises applying an AC voltage to the pair of electrodes or to another pair of electrodes, to concentrate the assemblies adjacent the pair of electrodes by dielectrophoresis.

5. The method as claimed in claim 1, wherein treating the biofluid to obtain the treated mixture comprises:
 introducing the biofluid to the suspension to provide a precursor mixture, wherein each of the plurality of nanoparticles is functionalized so that the nanoparticle is able to bind with the target biological entity to produce a bound nanoparticle-entity assembly;
 treating the precursor mixture to separate the bound nanoparticle-entity assemblies from nanoparticles not comprised in one of the bound nanoparticle-entity assemblies to provide the treated mixture.

6. A method as claimed in claim 1, wherein a dimension of each of the plurality of nanoparticles is greater than the lateral distance separating the pair of electrodes.

7. The method as claimed in claim 1, wherein characterizing a response of the sensing region to the nanoparticle sensing voltage to determine treated mixture characterizing data comprises identifying whether the sensing region exhibits ohmic behaviour.

8. The method as claimed in claim 1, wherein the nanoparticle sensing voltage is a constant voltage which induces a direct current between the electrodes.

9. The method as claimed in claim 1, wherein the plurality of nanoparticles comprises gold nanoparticles.

10. The method as claimed in claim 1, wherein the pair of electrodes comprise gold electrodes.

* * * * *